United States Patent
Lee et al.

(10) Patent No.: US 11,344,255 B2
(45) Date of Patent: May 31, 2022

(54) APPARATUS AND METHOD FOR MEASURING BODY FLUID

(71) Applicant: SAMSUNG ELECTRONICS CO., LTD., Suwon-si (KR)

(72) Inventors: So Young Lee, Daejeon (KR); Sang Kyu Kim, Yongin-si (KR); Hyun Seok Moon, Hwaseong-si (KR); Eui Seok Shin, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 342 days.

(21) Appl. No.: 16/549,610

(22) Filed: Aug. 23, 2019

(65) Prior Publication Data

US 2020/0060613 A1    Feb. 27, 2020

(30) Foreign Application Priority Data

Aug. 23, 2018   (KR) ........................ 10-2018-0098771

(51) Int. Cl.
*A61B 5/1455*  (2006.01)
*A61B 5/00*  (2006.01)
*A61B 5/145*  (2006.01)

(52) U.S. Cl.
CPC .......... *A61B 5/4878* (2013.01); *A61B 5/0059* (2013.01); *A61B 5/1455* (2013.01); *A61B 5/14507* (2013.01); *A61B 5/443* (2013.01); *A61B 5/486* (2013.01); *A61B 5/746* (2013.01)

(58) Field of Classification Search
CPC ... A61B 5/0059; A61B 5/4878; A61B 5/1455; A61B 5/443; A61B 5/746
See application file for complete search history.

(56) References Cited

U.S. PATENT DOCUMENTS

| | | | |
|---|---|---|---|
| 4,911,175 A | 3/1990 | Shizgal | |
| 6,587,701 B1 * | 7/2003 | Strane | A61B 5/14551 600/310 |
| 7,239,902 B2 * | 7/2007 | Schmitt | A61B 5/0059 600/310 |
| 9,110,008 B2 | 8/2015 | Baer et al. | |
| 2004/0171963 A1 | 9/2004 | Takehara | |
| 2006/0229527 A1 | 10/2006 | Takehara | |
| 2007/0118027 A1 * | 5/2007 | Baker | A61B 5/0059 600/310 |
| 2013/0144136 A1 * | 6/2013 | Rymut | A61B 5/0059 600/310 |

FOREIGN PATENT DOCUMENTS

EP   1452133 A1   9/2004
WO  2017005628 A1  1/2017

* cited by examiner

*Primary Examiner* — Eric F Winakur
(74) *Attorney, Agent, or Firm* — Sughrue Mion, PLLC (57) ABSTRACT

An apparatus for measuring a body fluid includes: an optical sensor configured to emit light onto an object, receive the light returning from the object, and measure a first intensity of a first wavelength and a second intensity of a second wavelength from the received light; and a processor configured to estimate a body fluid volume of the object based on the first intensity and the second intensity.

18 Claims, 11 Drawing Sheets

APPARATUS AND METHOD FOR MEASURING BODY FLUID

CROSS-REFERENCE TO RELATED APPLICATION(S)

This application claims priority from Korean Patent Application No. 10-2018-0098771, filed on Aug. 23, 2018, in the Korean Intellectual Property Office, the disclosure of which is incorporated herein by reference in its entirety.

BACKGROUND

1. Field

Apparatuses and methods consistent with example embodiments relate to non-invasively measuring a body fluid using an optical sensor.

2. Description of the Related Art

Recently, as our living environment has greatly improved along with better living conditions, individuals are increasingly interested in their health. Accordingly, a lot of research has been conducted to develop home medical devices to allow users to easily check their health condition at any time, and new products are being developed and brought to market at a rapid rate.

For the average person, the body fluid present in the human body is organically circulated and controlled, such that the volume of body fluid is maintained within a constant range. However, when a living body is afflicted with a disease, not only compositions of the body fluid but also the body fluid volume may be changed.

The body fluid volume may be measured by a method of using an isotope dilution and a method of using bioelectrical impedance. However, the method of using an isotope dilution has a drawback in that the method is an invasive measurement method, requiring huge costs and large equipment. Further, the method of using bioelectrical impedance is inconvenient in that users are required to attach electrodes, although the method is a non-invasive measurement method.

SUMMARY

Example embodiments address at least the above problems and/or disadvantages and other disadvantages not described above. Also, the example embodiments are not required to overcome the disadvantages described above, and may not overcome any of the problems described above.

Provided is an apparatus and method for non-invasively measuring a body fluid by using an optical sensor.

According to an aspect of an example embodiment, there is provided an apparatus for measuring a body fluid, the apparatus including: an optical sensor configured to emit light onto an object, receive the light returning from the object, and measure a first intensity of a first wavelength and a second intensity of a second wavelength from the received light; and a processor configured to estimate a body fluid volume of the object based on the first intensity and the second intensity.

The processor may calculate a ratio between the first intensity and the second intensity, and may estimate the body fluid volume of the object based on the calculated ratio between the first intensity and the second intensity.

The processor may be further configured to estimate the body fluid volume as a value that is proportional to the ratio between the first intensity and the second intensity.

The optical sensor may include: a single light source configured to emit the light in a predetermined wavelength range onto the object; a first photodetector configured to measure the first intensity by responding to the light of the first wavelength among light beams returning from the object; and a second photodetector configured to measure the second intensity by responding to the light of the second wavelength among the light beams returning from the object.

The optical sensor may include: a single light source configured to emit the light in a predetermined wavelength range onto an object; a first photodetector, which comprises a first filter configured to pass the light of the first wavelength among light beams returning from the object, and measures the first intensity of the light having passed through the first filter; and a second photodetector, which comprises a second filter configured to pass the light of the second wavelength among the light beams returning from the object, and measures the second intensity of the light having passed through the second filter.

The processor may predict a possibility of disease based on the estimated body fluid volume.

In response to an increase in the body fluid volume during a predetermined period of time being greater than or equal to a predetermined level, the processor may determine that the possibility of disease exists, and may generate a warning message.

The disease may be edema.

The processor may determine whether there is a deficiency of body water based on the estimated body fluid volume.

In response to the estimated body fluid volume being less than or equal to a predetermined threshold, the processor may determine that a body of the object is deficient in water, and may generate a recommendation message for fluid intake.

The processor may determine skin hydration based on the estimated body fluid volume.

In response to the estimated body fluid volume being less than or equal to a predetermined threshold, and the estimated body fluid volume remaining for a predetermined period of time, the processor may determine that skin hydration is poor, and may generate a recommendation message for moisturizing skin.

According to an aspect of another example embodiment, there is provided a method of measuring a body fluid, the method including: emitting light onto an object; receiving the light returning from the object; measuring a first intensity of a first wavelength and a second intensity of a second wavelength from the received light; and estimating a body fluid volume of the object based on the first intensity and the second intensity.

The estimating the body fluid volume may include calculating a ratio between the first intensity and the second intensity, and estimating the body fluid volume of the object based on the calculated ratio between the first intensity and the second intensity.

The method of measuring a body fluid may further include predicting a possibility of disease based on the estimated body fluid volume.

The predicting the possibility of disease may include, in response to an increase in the body fluid volume during a predetermined period of time being greater than or equal to a predetermined level, determining that the possibility of disease exists.

The method of measuring a body fluid may further include determining whether there is a deficiency of body water based on the estimated body fluid volume.

The determining whether there is a deficiency of body water may include, in response to the estimated body fluid volume being less than or equal to a predetermined threshold, determining that a body of the object is deficient in water.

The method of measuring a body fluid may further include determining skin hydration based on the estimated body fluid volume.

The determining of the skin hydration may include, in response to the estimated body fluid volume being less than or equal to a predetermined threshold, and the estimated body fluid volume volume remaining for a predetermined period of time, determining that skin hydration is poor.

BRIEF DESCRIPTION OF THE DRAWINGS

The above and/or other aspects will be more apparent by describing certain example embodiments, with reference to the accompanying drawings, in which.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented in hardware or software, or a combination thereof.

Figure 1:
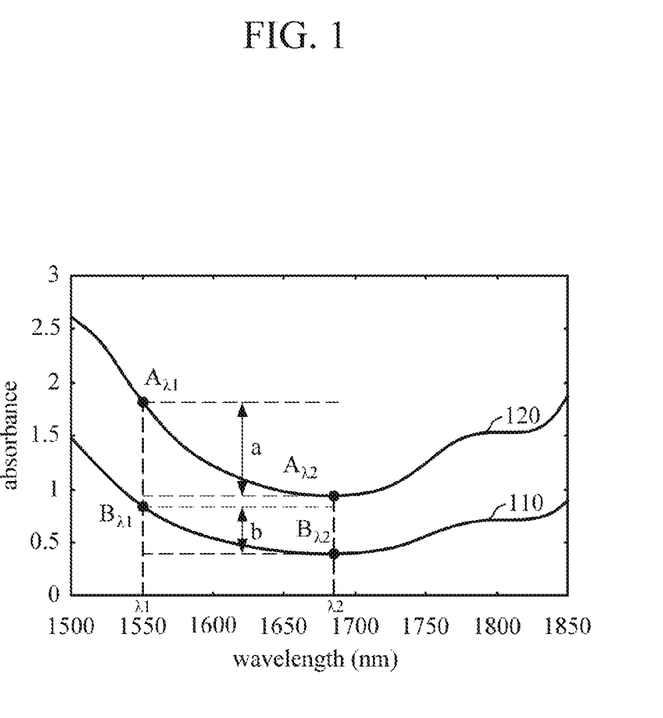
FIG. 1 is an exemplary diagram explaining a relationship between absorbance and an amount of water.

FIG. 1 is an exemplary diagram explaining a relationship between absorbance and an amount of water. An absorbance graph 110 of FIG. 1 is a graph showing water absorbance measured in a 1 mm cuvette filled with water; and an absorbance graph 120 is a graph showing water absorbance measured in a 2 mm cuvette filled with water.

Referring to FIG. 1, when measured in the 1 mm cuvette, water absorbance at a first wavelength λ1 (e.g., 1500 nm) is $B_{\lambda 1}$, and water absorbance at a second wavelength λ2 (e.g., 1700 nm) is $B_{\lambda 2}$; and when measured in the 2 mm cuvette, water absorbance at the first wavelength λ1 is $A_{\lambda 1}$, and water absorbance at the second wavelength λ2 is $A_{\lambda 2}$. As shown in FIG. 1, a difference 'a' between the absorbances $A_{\lambda 1}$ and $A_{\lambda 2}$ is about twice as large as a difference 'b' between the absorbances $B_{\lambda 1}$ and $B_{\lambda 2}$. That is, it can be seen that a difference between absorbances at two different wavelengths is proportional to the amount of water.

Figure 2:
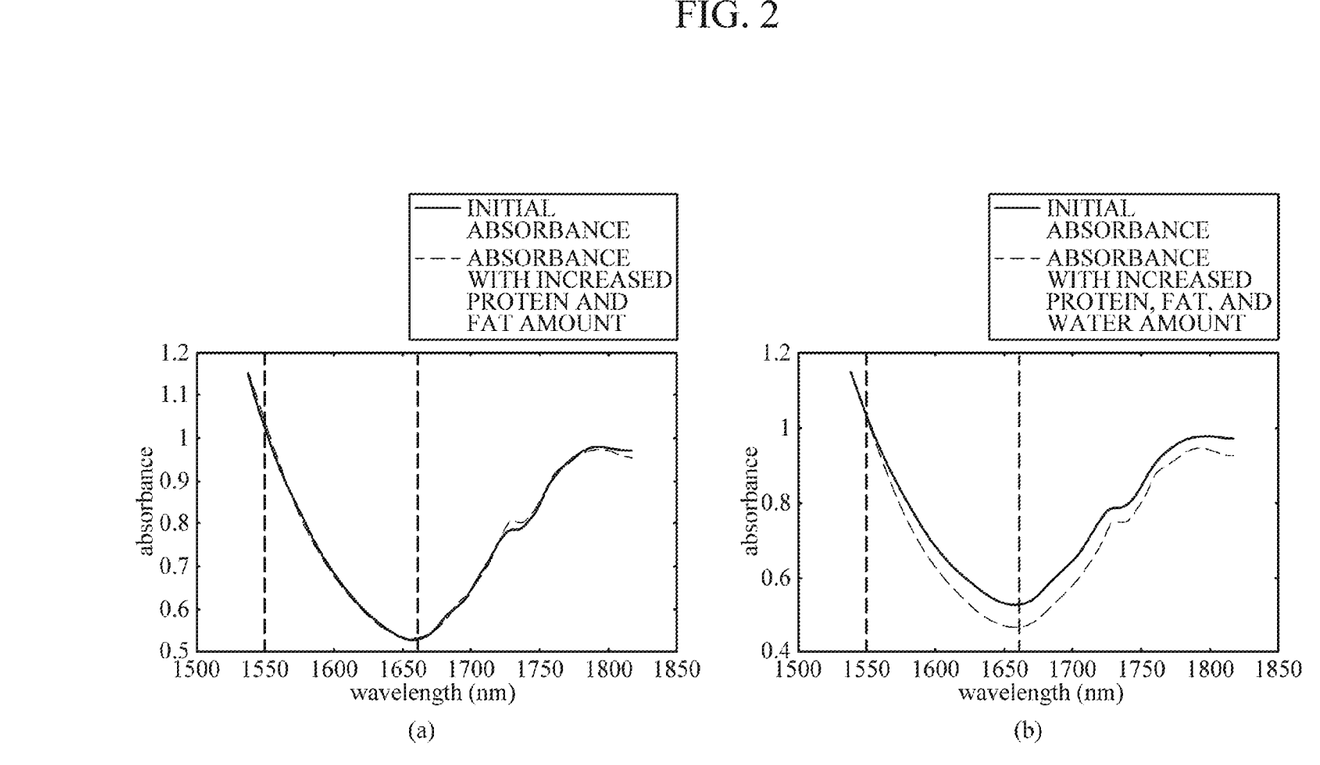
FIG. 2 is an exemplary diagram explaining a relationship between a difference between skin absorbances at two wavelengths and an amount of water.

FIG. 2 is an exemplary diagram explaining a relationship between a difference between skin absorbances at two wavelengths and an amount of water. A left graph (a) of FIG.

2 shows an absorbance graph when amounts of protein and fat increase; and a right graph (b) shows an absorbance graph when amounts of protein, fat, and water increase.

As illustrated in the left graph (a) of FIG. 2, when the amounts of protein and fat increase, a difference between absorbances at two wavelengths remains almost constant compared to an initial absorbance. By contrast, as illustrated in the right graph (b) of FIG. 2, when the amounts of protein, fat, and water increase, a difference between absorbances at two wavelengths increases compared to an initial absorbance.

That is, it can be seen that the difference between absorbances at two wavelengths is affected by a change in water rather than a change in protein or fat.

Since skin is composed of water, protein, fat, and a small amount of other substances, the difference between skin absorbances at two wavelengths is associated with an amount of water, i.e., a body fluid, rather than an amount of protein or fat in the skin.

Figure 3:
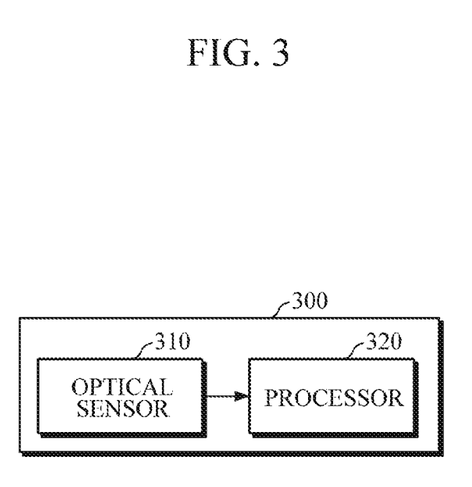
FIG. 3 is a block diagram illustrating an example of an apparatus for measuring a body fluid.

FIG. 3 is a block diagram illustrating an example of an apparatus for measuring a body fluid. The body fluid measuring apparatus of FIG. 3 is an apparatus for non-invasively estimating a body fluid of an object based on the relationship between the absorbance and the amount of water which is described above with reference to FIGS. 1 and 2, and may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 3, the body fluid measuring apparatus 300 includes an optical sensor 310 and a processor 320.

The optical sensor 310 may emit light onto an object and may receive reflected light returning from the object to measure reflected light intensities from the object. For example, the optical sensor 310 may measure a reflected light intensity at a first wavelength (hereinafter referred to as a first reflected light intensity) and a reflected light intensity at a second wavelength (hereinafter referred to as a second reflected light intensity) from an object, in which the first wavelength and the second wavelength may be different from each other.

To this end, the optical sensor 310 may include a light source and a photodetector. The optical sensor 310 may be implemented as a spectrometer.

The light source may emit light onto an object. In one embodiment, the light source may emit near infrared (NIR) light onto an object. However, wavelengths of light to be emitted by the light source may vary depending on a purpose of measurement or the types of analytes. Further, the light source is not necessarily a single light-emitting body, and may be formed as an array of a plurality of light-emitting bodies. The light source may include a light-emitting diode (LED), a laser diode, a fluorescent body, and the like. The light source may emit a plurality of lights having different wavelengths from each other. The plurality of lights may be emitted simultaneously or in a sequential manner.

The photodetector may receive reflected light returning from an object, and may measure intensities of the reflected light. In one embodiment, the photodetector may include a photo diode, a photo transistor (PTr), a charge-coupled device (CCD), and the like. The photodetector is not necessarily a single device, and may be formed as an array of a plurality of devices.

There may be various numbers and arrangements of the light source and the photodetector, and the number and arrangement thereof may vary according to a purpose of use of the optical sensor 310, and the size and shape of an electronic device in which the optical sensor 310 is mounted.

The processor 320 may estimate a body fluid volume of an object by using reflected light intensities of different wavelengths which are measured from the object by the optical sensor 310. In one embodiment, the processor 320 may calculate a ratio between the first reflected light intensity and the second reflected light intensity, and may estimate a body fluid volume of the object based on the calculated ratio between the first reflected light intensity and the second reflected light intensity.

As described above with reference to FIGS. 1 and 2, a difference between skin absorbances at two different wavelengths may be associated with a body fluid volume, and the difference between skin absorbances at two different wavelengths may be represented by the following Equation 1.

$$G_S = A_S(\lambda_1) - A_S(\lambda_2) = -\log\left(\frac{I_S(\lambda_1)}{I_0(\lambda_1)}\right) + \log\left(\frac{I_S(\lambda_2)}{I_0(\lambda_2)}\right) \quad \text{[Equation 1]}$$

Herein, $G_s$ denotes the difference between skin absorbances at two wavelengths, $\lambda_1$ and $\lambda_2$ denote the wavelengths, $A_s$ denotes the skin absorbance, $I_s$ denotes a reflected light intensity of skin, and $I_0$ denotes an incident light intensity.

In order to normalize the difference $G_s$ between skin absorbances at two wavelengths, a difference between water absorbances at two wavelengths may be used, in which the difference between water absorbances may be represented by the following Equation 2.

$$G_w = A_w(\lambda_1) - A_w(\lambda_2) = -\log\left(\frac{I_w(\lambda_1)}{I_0(\lambda_1)}\right) + \log\left(\frac{I_w(\lambda_2)}{I_0(\lambda_2)}\right) \quad \text{[Equation 2]}$$

Herein, $G_w$ denotes the difference between water absorbances at two wavelengths, $\lambda_1$ and $\lambda_2$ denote the wavelengths, $A_w$ denotes the water absorbance, $I_w$ denotes a transmitted light intensity of water, and $I_0$ denotes an incident light intensity.

Figure 8:
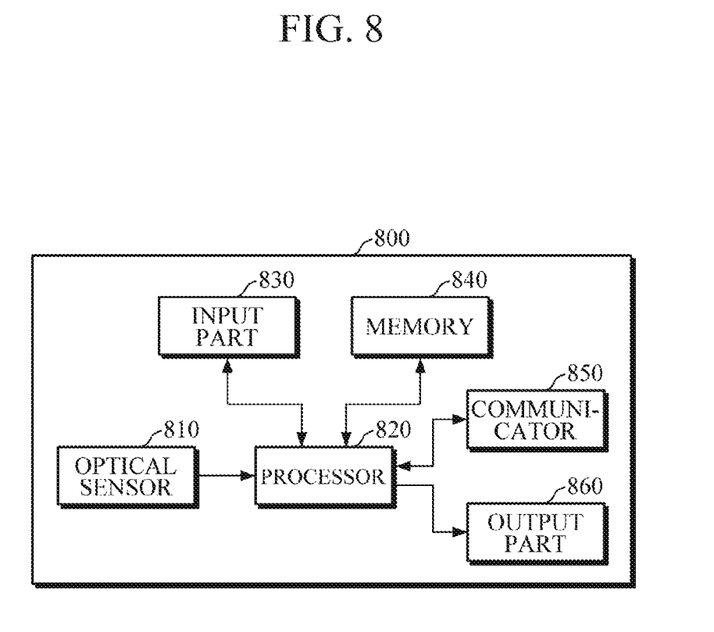
FIG. 8 is a diagram illustrating another example of an apparatus for measuring a body fluid.

The water absorbances may be pre-measured from reference spectrums, and the difference $G_w$ may be pre-calculated based on the water absorbances and stored in the body fluid measuring apparatus 300 (e.g., a memory 840 shown in FIG. 8). The processor 320 may retrieve the value of the difference $G_w$ from the memory 840 to normalize the difference $G_s$.

The difference $G_s$ between skin absorbances at two wavelengths may be normalized by subtracting the difference $G_w$ between water absorbances at two wavelengths from the difference $G_s$ between skin absorbances at two wavelengths, which may be represented by the following Equation 3.

$$G_S - G_w = -\log\left(\frac{I_S(\lambda_1)}{I_0(\lambda_1)}\right) + \log\left(\frac{I_S(\lambda_2)}{I_0(\lambda_2)}\right) + \log\left(\frac{I_w(\lambda_1)}{I_0(\lambda_1)}\right) - \quad \text{[Equation 3]}$$

-continued $$\log\left(\frac{I_w(\lambda_2)}{I_0(\lambda_2)}\right)$$
$$= \log\left(\frac{I_0(\lambda_1)}{I_S(\lambda_1)} \times \frac{I_S(\lambda_2)}{I_0(\lambda_2)} \times \frac{I_w(\lambda_1)}{I_0(\lambda_1)} \times \frac{I_0(\lambda_2)}{I_w(\lambda_2)}\right)$$
$$= \log\left(\frac{I_S(\lambda_2)}{I_S(\lambda_1)}\right) - \log\left(\frac{I_w(\lambda_2)}{I_w(\lambda_1)}\right)$$

Herein, $I_w(\lambda_1)$ and $I_w(\lambda_2)$ denote fixed values for normalization, such that the difference between skin absorbances at two wavelengths, which is normalized by G-G w, may be represented by the following Equation 4.

$$\text{Body Fluid Volume} \propto G_s - G_w \propto \log\left(\frac{I_S(\lambda_2)}{I_S(\lambda_1)}\right) \quad \text{[Equation 4]}$$

Accordingly, it can be seen that water in the skin (i.e., a body fluid volume) is proportional to the ratio between the reflected light intensities of two wavelengths.

That is, the processor 320 may estimate a body fluid volume of an object based on the ratio between the first light intensity and the second light intensity by using Equation 4.

The processor 320 may provide a predetermined function based on the estimated body fluid volume.

In one embodiment, the processor 320 may predict the possibility of disease, caused by body water imbalance such as edema and the like, based on the estimated body fluid volume, and may provide a warning message to a user. For example, in the case where a body fluid volume of an object sharply increases during a predetermined period of time, i.e., in the case where an increased volume of body fluid during a predetermined period of time is greater than or equal to a predetermined level, the processor 320 may determine that there is a possibility of disease such as edema and the like, and may generate a warning message and provide the message to a user through an output device.

In another embodiment, the processor 320 may determine whether there is a deficiency of body water based on the estimated body fluid volume, and may recommend that a user drink water. For example, in the case where a body fluid volume is less than or equal to a predetermined threshold, the processor 320 may determine that the body is deficient in water, and may generate a recommendation message for fluid intake and provide the message to a user through an output device.

In yet another embodiment, the processor 320 may determine skin hydration of an object based on the estimated body fluid volume, and may provide a recommendation based on the determined skin hydration. For example, in the case where a body fluid volume is less than or equal to a predetermined threshold, and the volume remains for a predetermined period of time, the processor 320 may determine that skin hydration is poor and may generate a recommendation message for moisturizing skin and provide the message to a user through an output device. In this case, the processor 320 may perform web browsing using a search engine to search for cosmetic products and the like which are good for moisturizing skin, and may provide the search result to a user through an output device.

Figure 4:
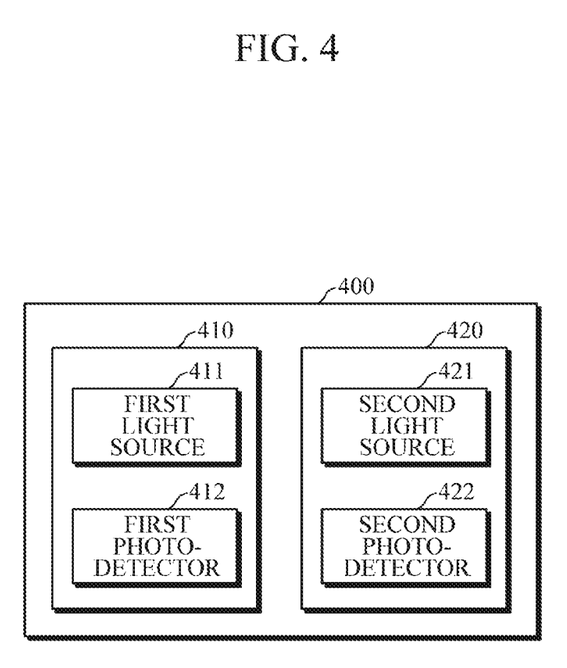
FIG. 4 is a block diagram illustrating an example of an optical sensor.

FIG. 4 is a block diagram illustrating an example of an optical sensor. The optical sensor 400 of FIG. 4 may be an example of the optical sensor 310 of FIG. 3.

Referring to FIG. 4, the optical sensor 400 according to an embodiment of the present disclosure may be formed as an array of optical sensors to measure reflected light intensities of different wavelengths from an object. As illustrated in FIG. 4, the optical sensor 400 may include a first optical sensor 410 and a second optical sensor 420. However, this is merely an example for convenience of explanation, and the number of optical sensors included in the optical sensor array is not specifically limited.

The first optical sensor 410 includes a first light source 411 which emits light of a first wavelength onto an object; and a first photodetector 412 which measures a first reflected light intensity by receiving reflected light of the first wavelength returning from the object.

The second optical sensor 420 includes a second light source 421 which emits light of a second wavelength onto an object; and a second photodetector 422 which measures a second reflected light intensity by receiving reflected light of the second wavelength returning from the object.

FIG. 4 illustrates the optical sensor 400 includes two light sources 411 and 421 and two photodetectors 412 and 422 to emit and detect lights having two different wavelengths, but the present embodiment is not limited thereto. For example, the optical sensor 400 may include a single light source that emits lights of different wavelengths, and the wavelength of the light emitted from the light source is adjusted by a temperature controller that controls the temperature of the light source.

Figure 5:
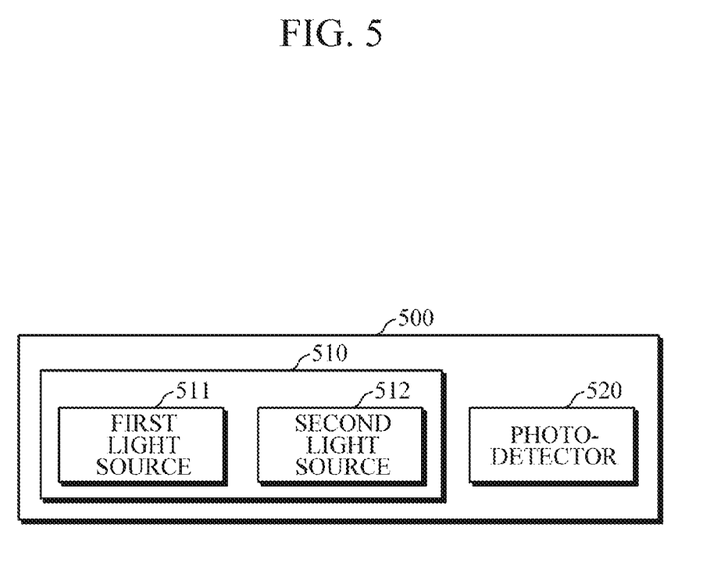
FIG. 5 is a block diagram illustrating another example of an optical sensor.

FIG. 5 is a block diagram illustrating another example of an optical sensor. The optical sensor 500 of FIG. 5 may be an example of the optical sensor 310 of FIG. 3.

Referring to FIG. 5, the optical sensor 500 according to another embodiment of the present disclosure includes a light source part 510 including a plurality of light sources 511 and 512, and a photodetector 520. While FIG. 5 illustrates an example where the light source part 510 includes two light sources, this is merely an example for convenience of explanation, and the number of light sources is not specifically limited.

The first light source 511 may emit light of a first wavelength onto an object, and the second light source 512 may emit light of a second wavelength onto an object. In this case, the first wavelength and the second wavelength may be different from each other.

The photodetector 520 may receive reflected light of the first wavelength and reflected light of the second wavelength, which return from the object, and may measure a first reflected light intensity and a second reflected light intensity.

For example, the first light source 511 and the second light source 512 may be driven in a time-division manner under the control of the processor to sequentially emit light onto an object. In this case, light source driving conditions, such as an emission time, a driving sequence, a current intensity, a pulse duration, and the like of the first light source 511 and the second light source 512 may be preset. The processor may control driving of each of the light sources 511 and 512 by referring to the light source driving conditions.

The photodetector 520 may sequentially detect the reflected light of the first wavelength and the reflected light of the second wavelength, which are sequentially emitted by the first light source 511 and the second light source 512 onto the object and return from the object, and may measure the first reflected light intensity and the second reflected light intensity.

Figure 6:
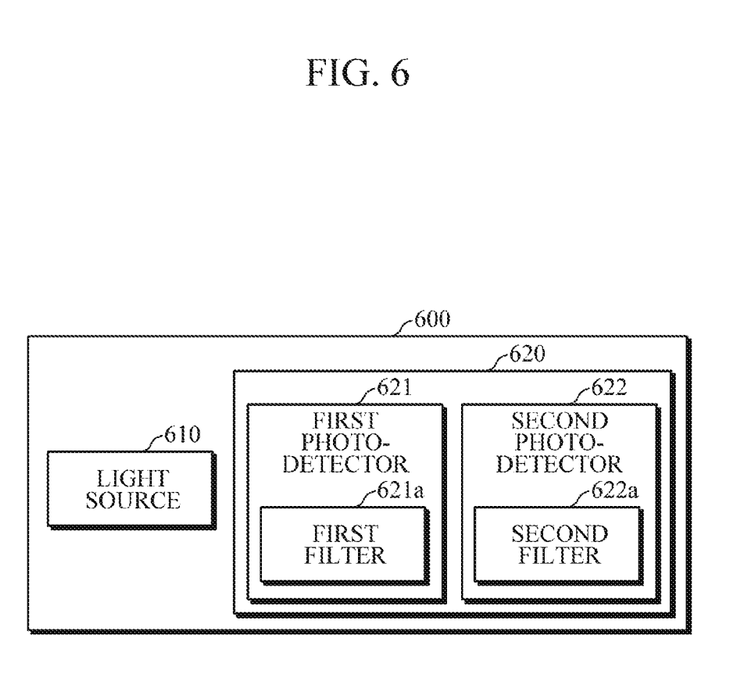
FIG. 6 is a block diagram illustrating yet another example of an optical sensor.

FIG. 6 is a block diagram illustrating yet another example of an optical sensor. The optical sensor 600 of FIG. 6 may be yet another example of the optical sensor 310 of FIG. 3.

Referring to FIG. 6, the optical sensor 600 according to yet another embodiment of the present disclosure includes a single light source 610 and a photodetector part 620. The photodetector part 620 includes a first photodetector 621 and a second photodetector 622. While FIG. 6 illustrates an example where the photodetector part 620 includes two photodetectors, this is merely an example for convenience of explanation, and the number of photodetectors is not specifically limited.

The single light source 610 may emit light in a predetermined wavelength range onto an object. In this case, the single light source 610 may emit light in a broad wavelength range including a near infrared range.

The photodetector part 620 may receive light in a predetermined wavelength range, which returns from an object, to measure a first reflected light intensity and a second reflected light intensity. To this end, the first photodetector 621 and the second photodetector 622 may have different response characteristics.

For example, the first photodetector 621 and the second photodetector 622 may be provided as photodiodes having different measurement ranges so as to respond to light of different wavelengths. Alternatively, a filter may be mounted on a front surface of any one of the first photodetector 621 and the second photodetector 622, or different filters (e.g., a first filter 621*a* and a second filter 622*a*) may be mounted on front surfaces of the two photodetectors 621 and 622, so as to respond to light of different wavelengths.

Embodiments of optical sensors for measuring reflected light intensities of different wavelengths from an object are described above with reference to FIGS. 4 to 6, which are merely exemplary and the optical sensor is not limited thereto. There may be various numbers and arrangements of the light source and the photodetector, and the number and arrangement thereof may vary according to a purpose of use of the optical sensor, and the size and shape of an electronic device in which the optical sensor is mounted.

Figure 7:
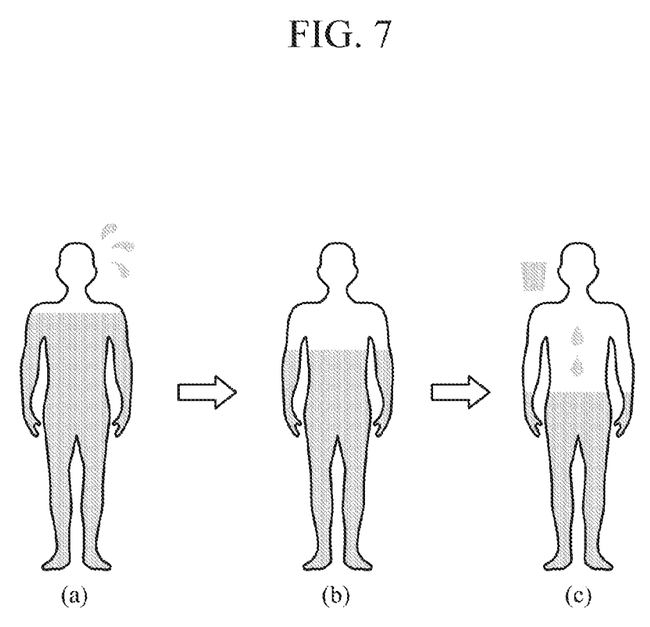
FIG. 7 is a diagram illustrating an example of a display for displaying a body fluid volume.

FIG. 7 is a diagram illustrating an example of a display for displaying a body fluid volume.

Referring to FIG. 7, a current body fluid volume may be displayed on an object having a human shape. In one embodiment, as the body fluid volume decreases, the body fluid volume may be displayed sequentially in the order of (a), (b), and (c) as illustrated in FIG. 7. For example, in the case where a body fluid volume currently decreases but is greater than or equal to a first threshold, a graphical object (a) is generated and displayed; in the case where a current body fluid volume is greater than or equal to a second threshold but is less than the first threshold, a graphical object (b) is generated and displayed; and in the case where a current body fluid volume is less than the second threshold, a graphical object (c) is generated and displayed. In this case, a graphical object (c) may include an indication of recommending a user to drink water.

FIG. 8 is a diagram illustrating another example of an apparatus for measuring a body fluid. The body fluid measuring apparatus 800 may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 8, the body fluid measuring apparatus 800 includes an optical sensor 810, a processor 820, an input part 830, a memory 840, a communicator 850, and an output part 860. Here, the optical sensor 810 and the processor 820 are the same as the optical sensor 310 and the processor 320 described above with reference to FIGS. 1 to 7, such that detailed description thereof will be omitted.

The input part 830 may receive input of various operation signals from a user. In one embodiment, the input part 830 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The memory 840 may store programs or commands for operation of the body fluid measuring apparatus 800, and may store data input to and output from the body fluid measuring apparatus 800. Further, the memory 840 may store data processed by the body fluid measuring apparatus 800, and data required for processing data of the body fluid measuring apparatus 800.

The memory 840 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the body fluid measuring apparatus 800 may operate an external storage medium, such as web storage and the like, which performs a storage function of the memory 840 on the Internet.

The communicator 850 may perform communication with an external device. For example, the communicator 850 may transmit an estimation result of a body fluid volume and a body fluid change trend to the external device. In addition, the communicator 850 may transmit data used by the body fluid measuring apparatus 800, a processing result data of the body fluid measuring apparatus 800, and the like to the external device, or may receive various data required or useful for estimating a body fluid volume from the external device.

In this case, the external device may be medical equipment using the data used by the body fluid measuring apparatus 800, the processing result data of the body fluid measuring apparatus 800, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 850 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output part 860 may output the data used by the body fluid measuring apparatus 800, the processing result data of the body fluid measuring apparatus 800, and the like. For example, the output part 860 may output the estimation result of a body fluid volume and the body fluid change trend, a result obtained by performing functions based on the estimated body fluid volume, e.g., a warning message for a possibility of disease, a recommendation message for water intake, a recommendation message for moisturizing skin, and the like. In one embodiment, the output part 860 may output the data used by the body fluid measuring apparatus 800, the processing result data of the body fluid measuring apparatus 800, and the like, by using at least one of an acoustic method, a visual method, and a tactile method. To this end, the output part 860 may include a display, a speaker, a vibrator, and the like.

Figure 9:
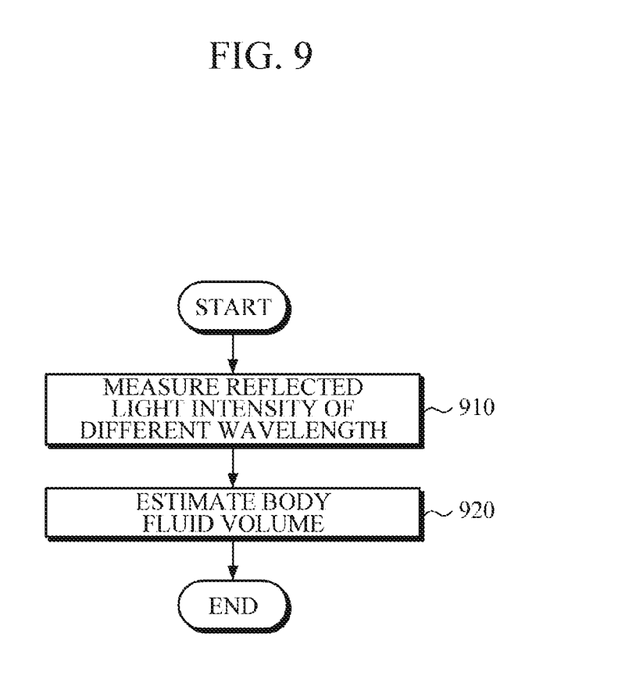
FIG. 9 is a flowchart illustrating an example of a method of measuring a body fluid.

FIG. 9 is a flowchart illustrating an example of a method of measuring a body fluid. The body fluid measuring method of FIG. 9 may be performed by the body fluid measuring apparatuses 300 and 800 of FIGS. 3 and 8.

Referring to FIG. 9, the body fluid measuring apparatus may emit light onto an object, and may receive reflected light returning from the object to measure reflected light intensities of different wavelengths from the object in operation 910. For example, the body fluid measuring apparatus may measure a first reflected light intensity of a first wavelength and a second reflected light intensity of a second wavelength from the object. In this case, the first wavelength and the second wavelength may be different from each other.

The body fluid measuring apparatus may estimate a body fluid volume of the object by using the reflected light intensities of different wavelengths in operation 920. For example, the body fluid measuring apparatus may calculate a ratio between the first reflected light intensity and the second reflected light intensity, and may estimate a body fluid volume of the object based on the calculated ratio between the first reflected light intensity and the second reflected light intensity. In this case, the body fluid measuring apparatus may use Equation 4.

Figure 10:
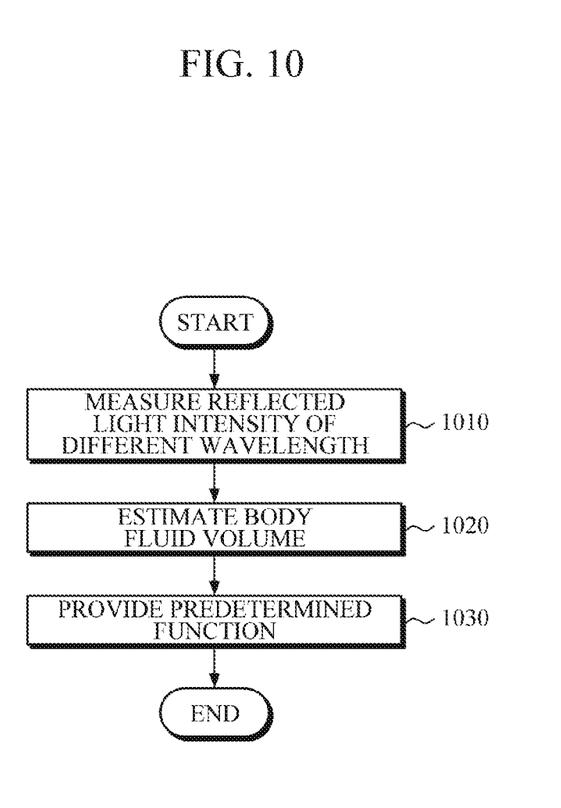
FIG. 10 is a flowchart illustrating another example of a method of measuring a body fluid.

FIG. 10 is a flowchart illustrating another example of a method of measuring a body fluid. The body fluid measuring method of FIG. 10 may be performed by the body fluid measuring apparatuses 300 and 800 of FIGS. 3 and 8.

Referring to FIG. 10, the body fluid measuring apparatus may emit light onto an object, and may receive reflected light returning from the object to measure reflected light intensities of different wavelengths from the object in operation 1010, and may estimate a body fluid volume of the object by using the reflected light intensities of different wavelengths in operation 1020.

The body fluid measuring apparatus may provide a predetermined function based on the estimated body fluid volume in operation 1030.

In one embodiment, the body fluid measuring apparatus may predict a possibility of disease, caused by body water imbalance such as edema and the like, based on the estimated body fluid volume, and may provide a warning message to a user. For example, in the case where a body fluid volume of an object sharply increases during a predetermined period of time, i.e., in the case where an increased volume of body fluid during a predetermined period of time is greater than or equal to a predetermined level, the body fluid measuring apparatus may determine that there is a possibility of disease such as edema and the like, and may generate a warning message based on the determination and provide the message to a user through an output device.

In another embodiment, the body fluid measuring apparatus may determine whether there is a deficiency of body water based on the estimated body fluid volume, and may recommend a user to drink water. For example, in the case where a body fluid volume is less than or equal to a predetermined threshold, the body fluid measuring apparatus may determine that the body is deficient in water, and may generate a recommendation message for fluid intake and provide the message to a user through an output device.

In yet another embodiment, the body fluid measuring apparatus may determine skin hydration of an object based on the estimated body fluid volume, and may provide a recommendation based on the determined skin hydration. For example, in the case where a body fluid volume is less than or equal to a predetermined threshold, and the volume remains for a predetermined period of time, the body fluid measuring apparatus may determine that skin hydration is poor and may generate a recommendation message for moisturizing skin and provide the message to a user through an output device. In this case, the body fluid measuring apparatus may perform web browsing using a search engine to search for cosmetic products and the like which are good for moisturizing skin, and may provide the search result to a user through an output device.

Figure 11:
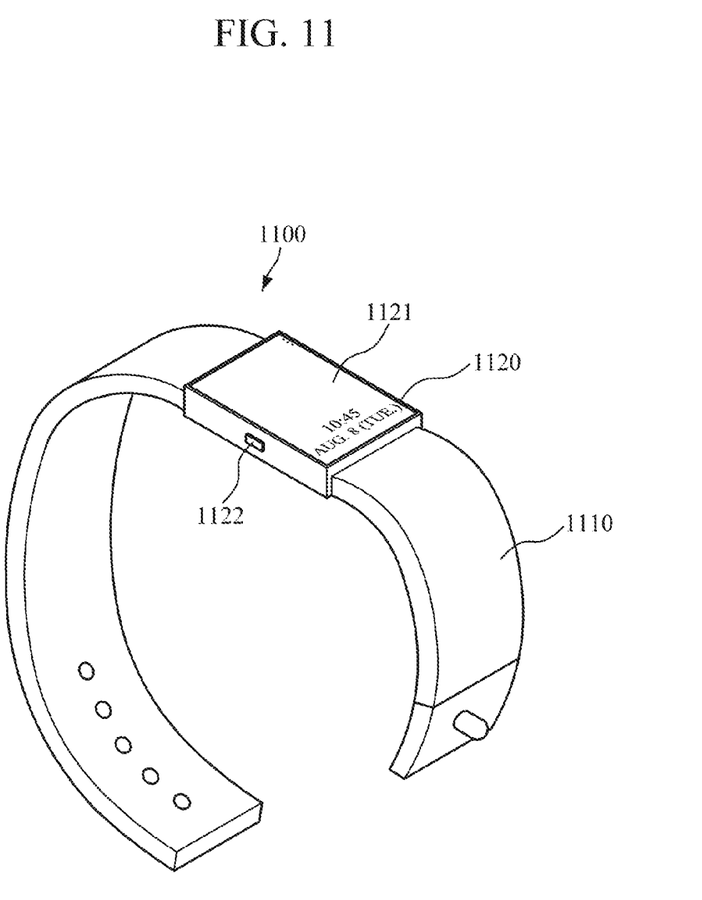
FIG. 11 is a diagram illustrating an example of a wrist-type wearable device.

FIG. 11 is a diagram illustrating an example of a wrist-type wearable device.

Referring to FIG. 11, the wrist-type wearable device 1100 includes a strap 1110 and a main body 1120.

The strap 1110 may be connected to both ends of the main body 1120 so as to be fastened in a detachable manner or may be integrally formed therewith as a smart band. The strap 1110 may be made of a flexible material to be wrapped around a user's wrist so that the main body 1120 may be worn on the wrist.

The main body 1120 may include the body fluid measuring apparatuses 300 and 800 described above. Further, the main body 1120 may include a battery which supplies power to the wrist-type wearable device 1100 and the body fluid measuring apparatuses 300 and 800.

An optical sensor may be mounted at the bottom of the main body 1120 to be exposed toward a user's wrist. Accordingly, when a user wears the wrist-type wearable device 1100, the optical sensor may naturally come into contact with the user's skin. In this case, the optical sensor may emit light onto an object and may receive light returning from the object to measure reflected light intensities.

The wrist-type wearable device 1100 may further include a display 1121 and an input part 1122 which are mounted at the main body 1120. The display 1121 may display data processed by the wrist-type wearable device 1100 and the body fluid measuring apparatuses 300 and 800, processing result data thereof, and the like. The input part 1122 may receive various operation signals from a user.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for measuring a body fluid, the apparatus comprising:
   an optical sensor configured to emit light onto an object, receive the light returning from the object, and measure a first intensity of a first wavelength and a second intensity of a second wavelength from the received light; and
   a processor configured to estimate a body fluid volume of the object based on the first intensity and the second intensity,
   wherein the processor is further configured to predict a possibility of disease based on the estimated body fluid volume.

2. The apparatus of claim 1, wherein the processor is further configured to calculate a ratio between the first intensity and the second intensity, and estimate the body fluid volume of the object based on the calculated ratio between the first intensity and the second intensity.

3. The apparatus of claim 2, wherein the processor is further configured to estimate the body fluid volume as a value proportional to the ratio between the first intensity and the second intensity.

4. The apparatus of claim 1, wherein the optical sensor comprises:
   a single light source configured to emit the light in a predetermined wavelength range onto the object;
   a first photodetector configured to measure the first intensity by responding to the light of the first wavelength among light beams returning from the object; and
   a second photodetector configured to measure the second intensity by responding to the light of the second wavelength among the light beams returning from the object.

5. The apparatus of claim 1, wherein the optical sensor comprises:
   a single light source configured to emit the light in a predetermined wavelength range onto the object;
   a first photodetector, which comprises a first filter configured to pass the light of the first wavelength among light beams returning from the object, and measures the first intensity of the light having passed through the first filter; and
   a second photodetector, which comprises a second filter configured to pass the light of the second wavelength among the light beams returning from the object, and measures the second intensity of the light having passed through the second filter.

6. The apparatus of claim 1, wherein in response to an increase in the body fluid volume during a predetermined period of time being greater than or equal to a predetermined level, the processor is further configured to determine that the possibility of disease exists, and generate a warning message.

7. The apparatus of claim 1, wherein the disease is edema.

8. The apparatus of claim 1, wherein the processor is further configured to determine whether there is a deficiency of body water based on the estimated body fluid volume.

9. The apparatus of claim 8, wherein in response to the estimated body fluid volume being less than or equal to a predetermined threshold, the processor is further configured to determine that a body of the object is deficient in water, and generate a recommendation message for fluid intake.

10. The apparatus of claim 1, wherein the processor is further configured to determine skin hydration based on the estimated body fluid volume.

11. The apparatus of claim 10, wherein in response to the estimated body fluid volume being less than or equal to a predetermined threshold, and the estimated body fluid volume remaining for a predetermined period of time, the processor is further configured to determine that skin hydration is poor, and generates a recommendation message for moisturizing skin.

12. A method of measuring a body fluid, the method comprising:
    emitting light onto an object;
    receiving the light returning from the object;
    measuring a first intensity of a first wavelength and a second intensity of a second wavelength from the received light;
    estimating a body fluid volume of the object based on the first intensity and the second intensity; and
    predicting a possibility of disease based on the estimated body fluid volume.

13. The method of claim 12, wherein the estimating the body fluid volume comprises calculating a ratio between the first intensity and the second intensity, and estimating the body fluid volume of the object based on the calculated ratio between the first intensity and the second intensity.

14. The method of claim 12, wherein the predicting the possibility of disease comprises, in response to an increase in the body fluid volume during a predetermined period of time being greater than or equal to a predetermined level, determining that the possibility of disease exists.

15. The method of claim 12, further comprising determining whether there is a deficiency of body water based on the estimated body fluid volume.

16. The method of claim 15, wherein the determining whether there is the deficiency of body water comprises, in response to the estimated body fluid volume being less than or equal to a predetermined threshold, determining that a body of the object is deficient in water.

17. The method of claim 12, further comprising determining skin hydration based on the estimated body fluid volume.

18. The method of claim 17, wherein the determining the skin hydration comprises, in response to the estimated body fluid volume being less than or equal to a predetermined threshold, and the estimated body fluid volume remaining for a predetermined period of time, determining that skin hydration is poor.

* * * * *